United States Patent
Wiest et al.

(10) Patent No.: US 7,395,720 B2
(45) Date of Patent: Jul. 8, 2008

(54) APPARATUS FOR SECURING A MEASURING SENSOR ON A PIPELINE

(75) Inventors: Achim Wiest, Weil am Rhein (DE); Andreas Berger, Therwil (CH); Patrick Oudoire, Soultz (FR)

(73) Assignee: Endress + Hauser Flowtec AG, Reinach (CH)

( * ) Notice: Subject to any disclaimer, the term of this patent is extended or adjusted under 35 U.S.C. 154(b) by 255 days.

(21) Appl. No.: 11/260,220

(22) Filed: Oct. 28, 2005

(65) Prior Publication Data

US 2006/0090570 A1     May 4, 2006

(30) Foreign Application Priority Data

Oct. 28, 2004   (DE)   ........................ 10 2004 052 489

(51) Int. Cl.
*F16B 31/02*   (2006.01)
(52) U.S. Cl. .......................................... 73/761; 73/856
(58) Field of Classification Search ........... 73/760–761, 73/856
See application file for complete search history.

(56) References Cited

U.S. PATENT DOCUMENTS

| | | | | | |
|---|---|---|---|---|---|
| 3,938,547 | A | * | 2/1976 | Jones | ......................... 137/488 |
| 4,499,347 | A | * | 2/1985 | Richards | ................. 200/81.9 M |
| 4,761,024 | A | * | 8/1988 | Ewen | ........................... 285/93 |
| 4,921,386 | A | * | 5/1990 | McArthur | ................ 414/22.51 |
| 5,066,053 | A | * | 11/1991 | Miller | ......................... 285/373 |
| 5,131,278 | A | * | 7/1992 | Baumoel | ................. 73/861.18 |
| 5,410,920 | A | * | 5/1995 | Westwick | .................. 73/866.5 |
| 6,758,098 | B1 | * | 7/2004 | Nunnelee | ..................... 73/760 |

FOREIGN PATENT DOCUMENTS

| | | |
|---|---|---|
| EP | 0 773 431 A2 | 5/1997 |
| EP | 1 396 707 A1 | 3/2004 |
| JP | 08 184425 A | 12/1994 |
| SU | 769336 A1 | 10/1980 |

* cited by examiner

*Primary Examiner*—Max Noori
(74) *Attorney, Agent, or Firm*—Bacon & Thomas, PLLC

(57) ABSTRACT

An apparatus for securing a measuring sensor on a pipeline. The mounting-housing is positionable on the pipeline, with the mounting-housing being embodied, and coordinated with the measuring sensor, in such a manner that a force, which acts on the mounting-housing in the direction of the pipeline, acts at least partly on the on the measuring sensor in the direction of the pipeline; and that at least one screw unit is provided, via which an adjustable force can be exerted on the mounting-housing in the direction of the pipeline.

7 Claims, 4 Drawing Sheets

APPARATUS FOR SECURING A MEASURING SENSOR ON A PIPELINE

Figure 1:
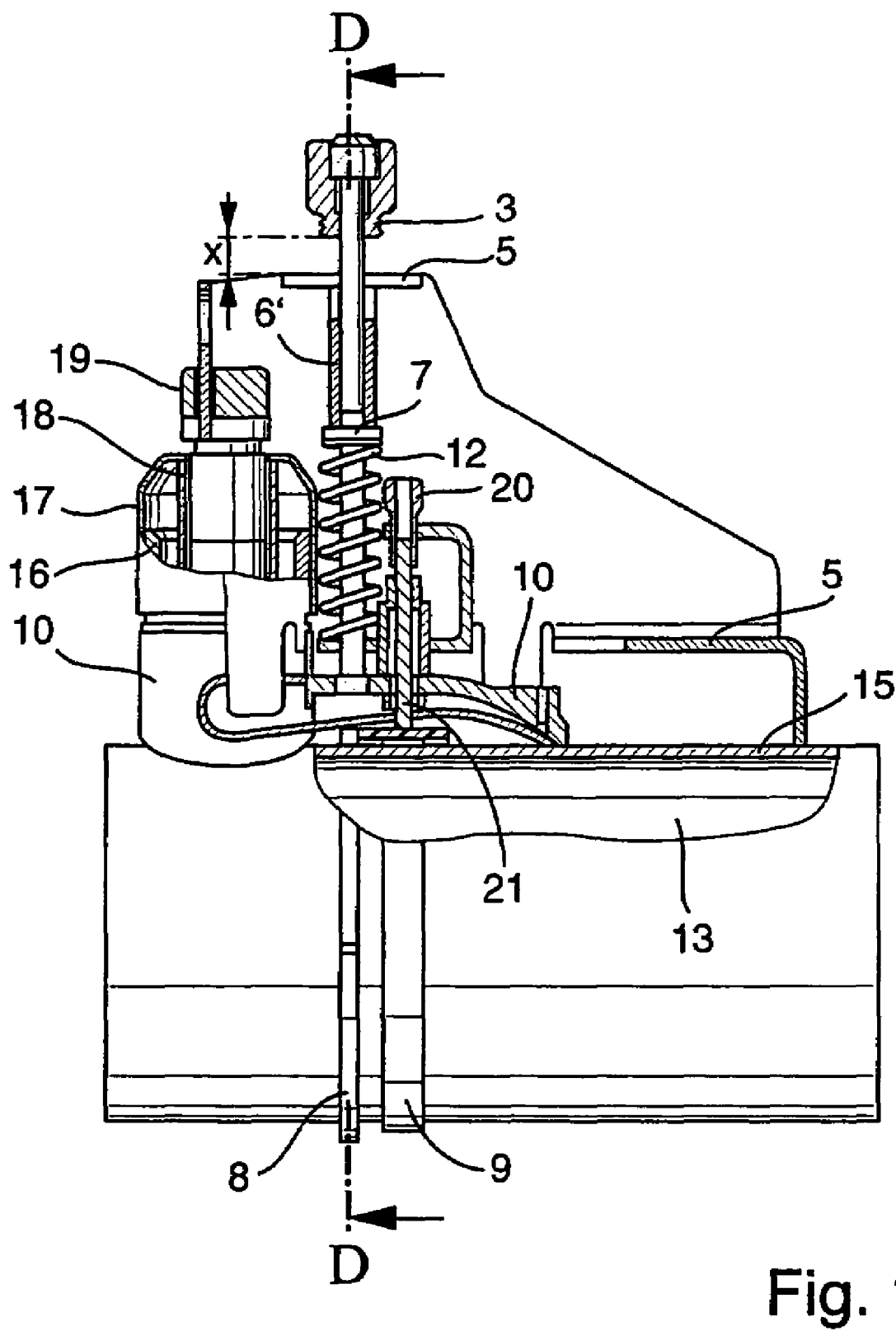

The invention relates to an apparatus for securing a measuring sensor on a pipeline.

In the case of so-called clamp-on ultrasonic flow measuring devices, the flow, for instance flow rate, of a medium through a pipeline can be determined by measuring travel time. To do this, ultrasonic waves are radiated into the pipeline at a certain angle, and then detected. From the travel time of the waves, flow can then be determined. This is a case of a contactlessly-functioning measuring principle, with a great advantage being that the required measuring sensors can be subsequently mounted on already-installed pipelines.

Positioning units, which permit the positioning of the sensors on pipelines, are manufactured and sold by the assignee. It is important that no air layer be present between the ultrasonic sensors and the pipelines, because such a layer would be extremely detrimental to the coupling of the ultrasonic waves into the pipeline. For this reason, a layer of grease is usually applied to the active surfaces of the ultrasonic sensors. Normally, a force of 10 N is enough to press the sensors sufficiently close to the pipeline. It is also possible to use coupling layers made of elastomer or metal between the sensor and pipeline. Such layer do, however, require a distinctly higher contact pressure, which is associated with multiple problems. For one, an electronics package, or at least an electric connection extending from the end of the sensor facing away from the pipeline, is normally to be found on the sensor. For this reason, it is usually not possible to exert the contact pressure directly above the contact point of the sensor on the pipeline. Thus, an appropriate application point for the contact pressure must be found, and it must be assured that the force to be applied does not produce another reaction force, which e.g. acts on the positioning unit, and leads to unfavorable consequences. Thus it must especially be avoided that the shape of the pipeline is influenced by a unilateral application of force. Because the travel time also depends on the separation, that is, on the diameter of the pipe, this diameter cannot be changed in an undefined manner. Moreover, as much as possible, it should be avoided that, on site, excessive force can be applied by the user.

Therefore, an object of the invention is to provide an apparatus for securing a sensor utilizing a predetermined contact force, wherein production of a force acting unilaterally against the pipeline is avoided.

This object is achieved by the invention in that a mounting-housing, which is positionable on the pipeline, is provided, with the housing being embodied, and coordinated with the measuring sensor, in such a manner that a force, acting on the mounting-housing in the direction of the pipeline, acts at least partly on the measuring sensor in the direction of the pipeline, and that at least one screw unit is provided, via which an adjustable force can be exerted on the mounting-housing in the direction of the pipeline. In the following, the term "screw unit" means a unit, via which the execution of a movement in a direction or in a plane (for example the turning of a screw) leads to an exertion of force in a plane or direction essentially perpendicular thereto. The unit is preferably associated with a self-limiting feature. In the simplest case, it is a screw. The radial turning of the screw leads to a motion perpendicular to the plane of rotation.

The invention is thus composed such that the measuring sensor is pressed against the pipeline via a mounting-housing, with it being accordingly possible that, through an appropriate embodiment of the mounting-housing, particular requirements can be provided, or a balancing of forces effected. A screw unit then exerts the required pressure. The mounting-housing is preferably embodied such that a section of the housing rests on the roof of the measuring sensor, or on the side of the measuring sensor facing away from the pipeline, as the case may be. The mounting-housing thus surrounds the measuring sensor at least partially, or a section of it lies on the sensor.

An embodiment of the apparatus therefore includes that the mounting-housing is coordinated with the measuring sensor in such a way that the mounting-housing lies at least partially on the roof of the measuring sensor. The roof forms the end of the measuring sensor facing away from the pipeline, on which the pressure is to be exerted, so that the sensor lies as closely as possible against the pipeline. Alternatively, the mounting-housing can also partially surround the measuring sensor, insofar as the embodiment is such that a holding area is present on the sensor.

An embodiment of the apparatus of the invention provides that the mounting-housing and the screw unit are embodied, and coordinated with one another, in such a manner that a turning of the screw unit into the mounting-housing exerts a force on the mounting-housing essentially in the direction of the pipeline. Thus the screw unit is screwed into the mounting-housing and, in this way, the required force is exerted. The expressions "turning into", "screwing into" and "rotating into" all are understood, in general, to mean that the screw unit experiences a movement in one plane, and that the screw unit thereby exerts a force in a plane perpendicular thereto. The screw unit is thus moved inwards, or, especially, it is displaced toward the pipeline.

An embodiment of the apparatus of the invention includes that the screw unit exerts a force on at least one spring, essentially in the direction of the pipeline. Thus, the screw unit applies the force, preferably during or after the screwing-in, first onto a spring. This has the advantage that the force effectively exerted on the mounting-housing and thus on the measuring sensor, can, through the embodiment of the spring, be adjusted and, therefore, predetermined. To this belongs also an embodiment wherein, between the spring and the screw unit, at least one cross piece is provided. Thus the screw unit presses against the cross piece, and, by means of this, the spring is correspondingly compressed.

An embodiment of the apparatus of the invention includes that the spring is a component of the screw unit. Thus the screw unit is specially embodied such that a spring is integrated into it. Therefore the screw unit can be screwed into the mounting-housing in the manner of a usual screw, and the screw simultaneously exerts a pressure predetermined by the spring integrated within it.

An embodiment of the device of the invention provides that, in the mounting-housing, at least one movable bracket is provided, and that the bracket and the screw unit are embodied such that they coordinate with one another, and such that a screwing-in of the screw unit in the direction of the pipeline produces a force on the bracket, which force is at least partially directed away from the pipeline. Preferably the bracket has a passageway, through which the screw unit is directed. In the simplest case, the passageway is a corresponding threaded passage. Thus, in the region of the passageway, the screw unit extends through the bracket.

An embodiment of the apparatus of the invention includes that at least one chain is provided, which can be placed radially around the pipeline, and which can be connected to the bracket. Through the use of this chain, the moments of force are balanced such that the screw unit can be secured to the mounting-housing, and the contact pressure can be applied to the measuring sensor such that e.g. deformations of the pipeline and other undesired effects are avoided. The term "chain" is meant to include a cable or a strap, as well.

An embodiment of the apparatus of the invention also provides that at least one limiting unit is provided, which limits the screwing-in of the screw unit. Through this embodiment, it is assured that excessive force cannot be applied. Thus, through the limiting unit, a maximum exertable contact force is predetermined.

An embodiment of the apparatus of the invention includes that the limiting unit is embodied such that the limiting of the screwing-in of the screw unit acts radially. Thus, the contact force is not influenced, as no "limiting force" acts in the direction of the pipeline. Here, the term "radially" indicates the direction of rotation of the screw unit. The contact force acts perpendicularly to this radial plane.

An embodiment of the apparatus of the invention provides that the screw unit is embodied such that at least one display element is provided, which indicates when a predeterminable force has been produced with the screw unit.

An embodiment of the device of the invention provides that the measuring sensor is an ultrasonic sensor. A clamp-on ultrasonic sensor is described above.

Figure 2:
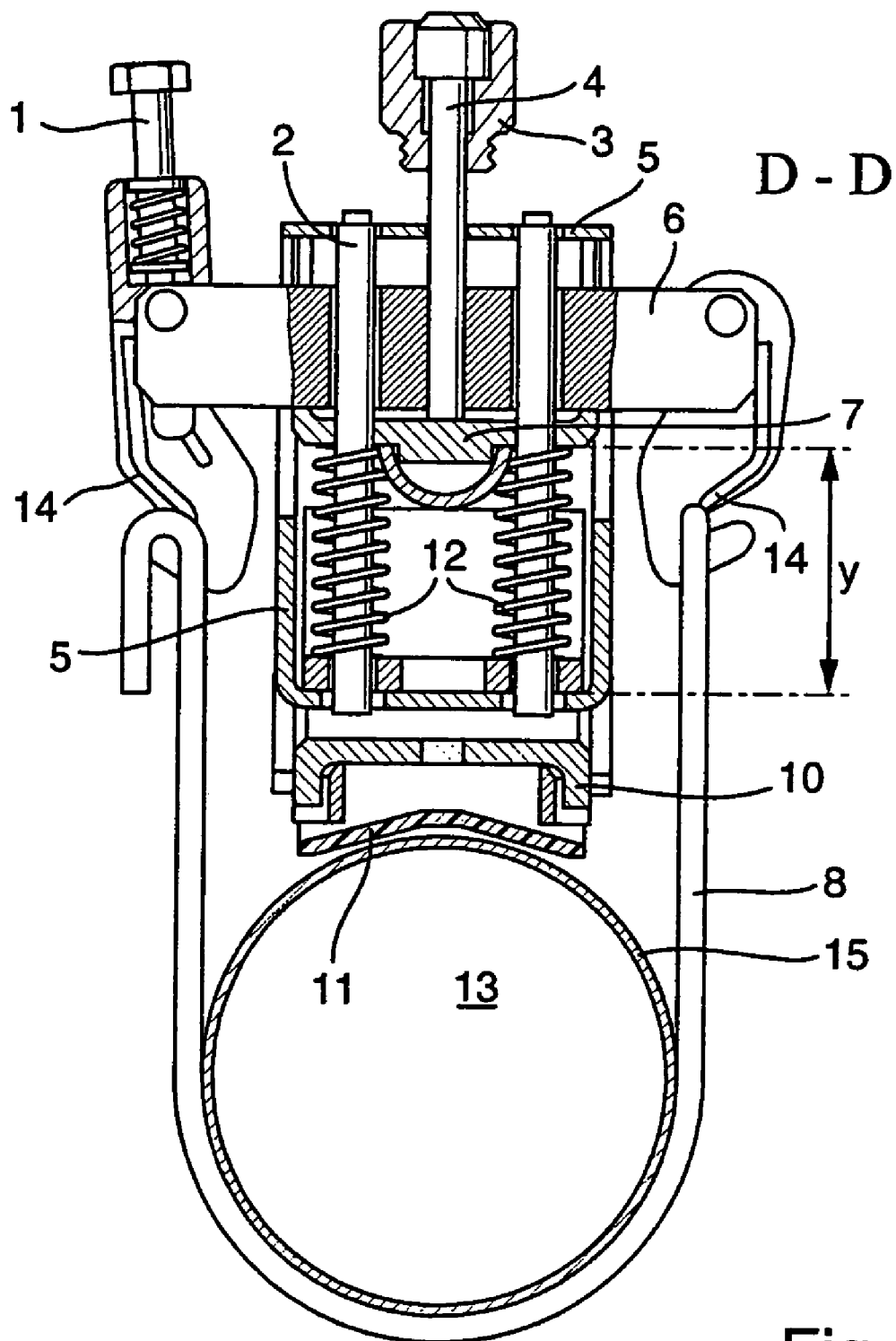
Figure 3:
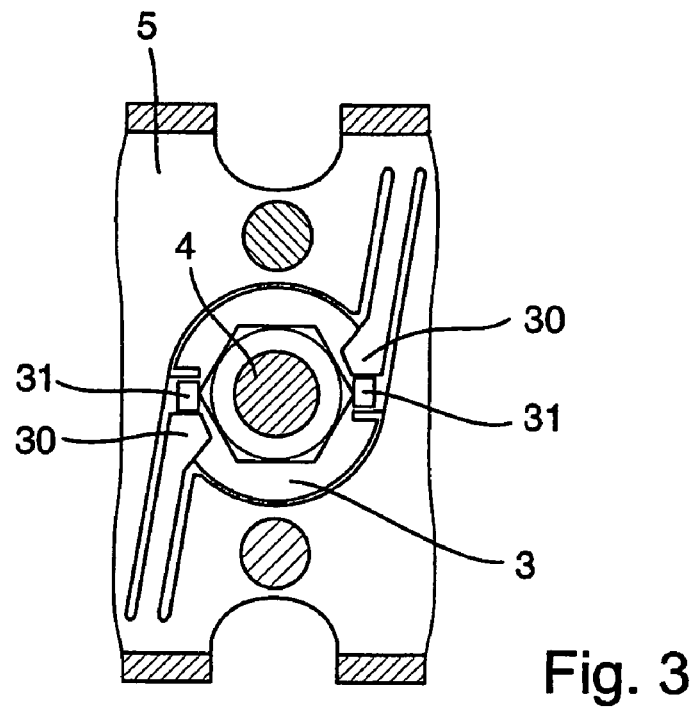
Figure 4:
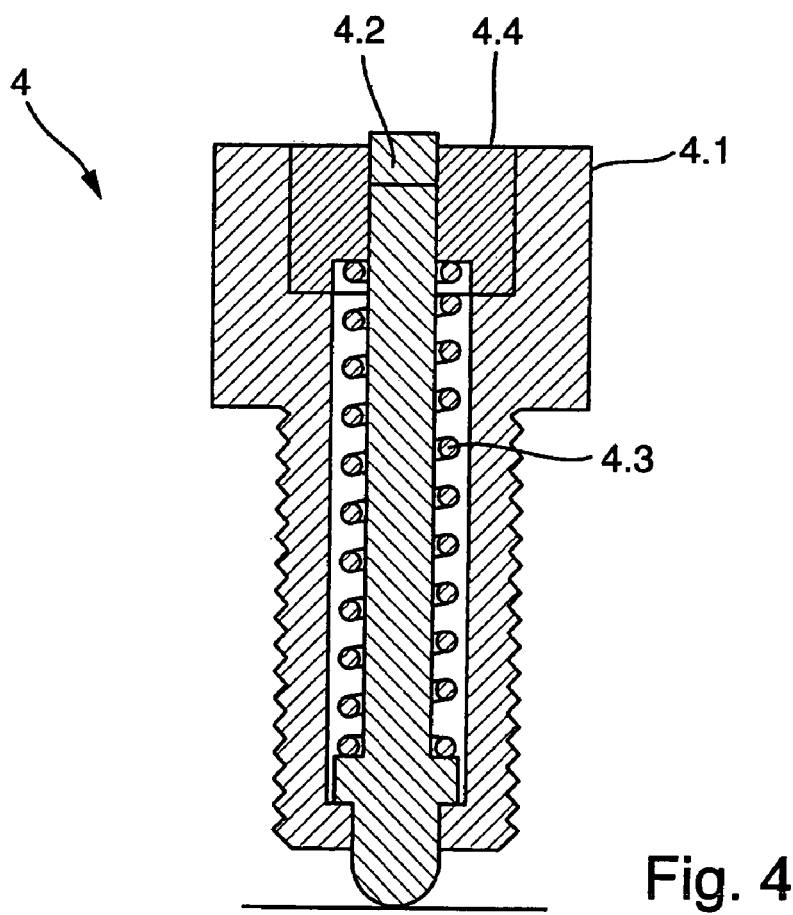
Figure 5:
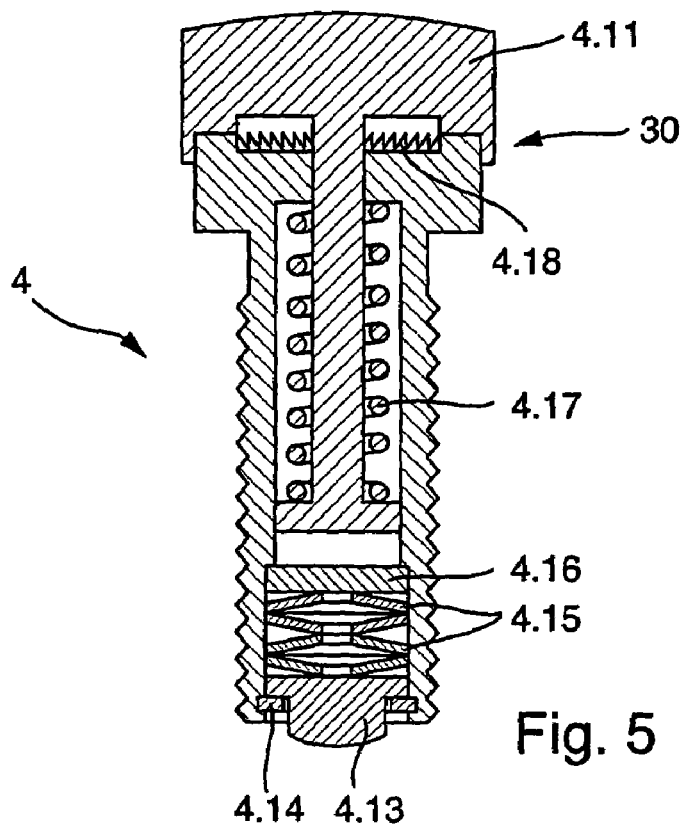

The invention will now be described in greater detail on the basis of the drawings, the figures of which show as follows:

FIG. 1 a section through a side view of a pipeline, on which a measuring sensor is secured by means of an apparatus of the invention;

FIG. 2 a section taken perpendicular to the illustration in the preceding figure, FIG. 1;

FIG. 3 a detail view (plan view) of a part of the mounting-housing;

FIGS. 4 and 5 illustrations of two different embodiments of the screw unit; and

Figures 6A, 6B:
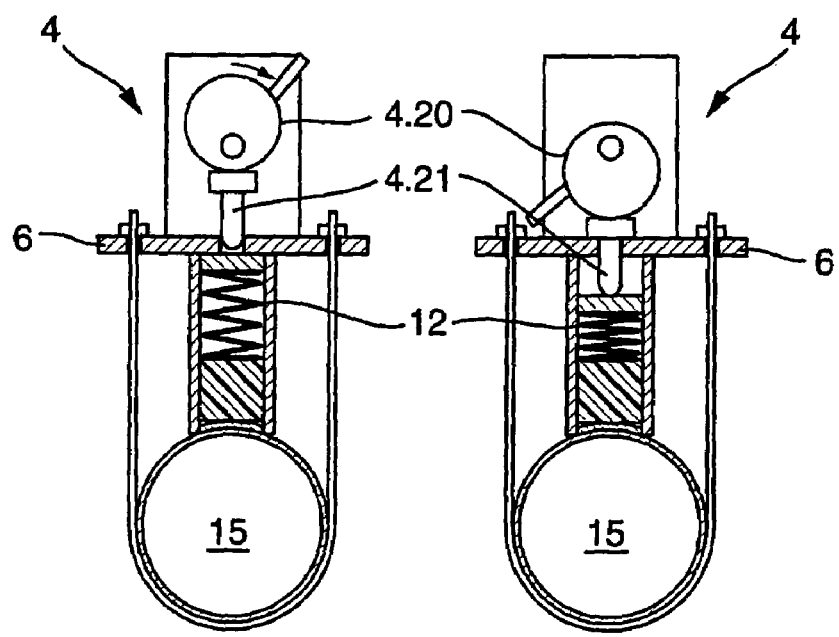

FIGS. 6a and 6b a further embodiment of the screw unit.

FIG. 1 shows a section through the pipeline 15 with an apparatus of the invention, and FIG. 2 is a section perpendicular thereto, taken along the plane D. The following description relates to both drawings. The measuring sensor 16 is positioned on the pipeline 15 by means of a standard retainer 10 produced and sold by the assignee. Retainer 10 is secured to the pipeline 15 via a band-clamp 9, and, in the retainer 10, the measuring sensor 16 is inserted into a tubular structure. Because the measuring sensor 16 in this example is an ultrasonic sensor, it is important that no air gap be present between the sensor 16 and the pipeline 15, thus that the sensor 16 is pressed directly onto the pipeline 15. For this purpose, it is possible to apply grease to the sensor 16, or, as in this case, to provide between the sensor 16 and the pipeline 15 a coupling mat 11 made of an elastomer or a metal film.

One such mat of an elastomer normally requires a higher contact pressure of up to 0.5 MPa. The application of this force is difficult e.g. because of the electronic superstructure 19, which is normally present on the roof 17 of the sensor; that is, the pressure cannot be applied directly to the sensor roof 17. Therefore, the apparatus of the invention is necessary. This includes a mounting-housing 5 placed on the pipeline 15. In the embodiment illustrated, the mounting-housing 5 rests on two points, with, in this way, a separation of forces also being realized. For a simpler installation, here the housing 5 is secured to the standard retainer 10 via a mounting screw 20.

The mounting-housing 5 has a bracket 6, which can be shifted on guide bolts 2 perpendicularly to the longitudinal axis of the pipeline 15. A chain 8 is secured to the bracket 6 at the quick-locking securement catches 14. The quick-locking feature is in turn an advantage for the simple mounting. Chain 8 is securely tightened via the tightening screw 1. A threaded passage 6' goes through the bracket 6 to provide a passageway, through which the screw unit 4, in turn, is directed. The threaded passageway 6' and the screw unit 4 are coordinated with one another such that a screwing-in of the screw unit 4 exerts a force on the bracket 6 in the opposite direction, that is, the bracket is pressed away from the pipeline 15. Since this force, however, acts oppositely to the tightened chain 8, bracket 6 results in a very stable construction, which, above all, produces no other forces outside of this bracket-chain axis.

Thus, the screw unit 4 is essentially rotated against a stable and rigid wall. As it is screwed in, screw unit 4 presses against the cross piece 7, below which, in this instance, two springs 12 are located. Through the embodiment of the springs 12, the pressure is set, which, in turn, acts on the housing-mounting 5, since the springs 12 rest, on their ends opposite cross piece 7, on an appropriately embodied section of the mounting-housing 5. Thus, through the screw unit 4, a pressure acts on the housing-mounting 5 in the direction of the pipeline 15. Because the mounting-housing 5 lies partially on the measuring sensor 16 (a section of the mounting-housing rests on the edge of the roof of the sensor), the pressure also acts on the sensor 16, and thus also presses this against the pipeline 15. The required stability, in order that e.g. no tilting moment is produced, results from the bracket 6 in connection with the chain 8, which together produce a stable plane.

The spring-constant of the springs 12, and the screw-in depth of the screw unit 4 are essentially responsible for determining a well-defined force, that is, so that excessive force is not used. Since the screwing-in of the screw unit 4 occurs on-site, a limiting unit 30 is provided, which can be seen in the plan view in FIG. 3. FIG. 3 shows the upper section of the mounting-housing 5 with the screw unit 4. The limiting unit 30 is composed of two spring-like sections 31 of the mounting-housing 5, which prevent the correspondingly embodied screw unit 4 from rotating further. If the screw unit 4 is screwed out, then the limiting unit 30 no longer provides any hindrance. Since the limiting unit 30 forms a radial abutment, consequently, then also no undefined compressive forces act in the direction of the pipeline 15.

FIG. 4 shows a special embodiment of the screw unit 4. The use of this type of screw is not limited to the invention, but rather can be generally used in solutions to similar problems. In this instance, screw unit 4 is composed of a member 4.1 in which a movable display element 4.2—a spring-loaded pin—and a spring 4.3 are located along the rotational axis of the screw unit 4. Closure of the screw unit 4 is achieved using a grub screw 4.4. Display element 4.2—a rod provided with markings on its upper end—is arranged in a cavity of the member 4.1 of the screw unit, such that it can be displaced.

On its lower end, the member 4.1 has an opening so that the spring 4.3 can press the display element 4.2 out of this opening. If the screw unit 4 is rotated, and a surface (represented here by the line) is located behind the screw-in range, then the display element 4.2 is pressed against the surface, and thus, at the same time, is pressed out of the other opening of the member 4.1 through the grub screw 4.4. If the screw unit 4 is screwed in so far that the member 4.1 itself touches the surface (illustrated here by the wide lower face of the member 4.1), and so that a further rotation would involve a penetration into the surface (this would also imply that a greater force/greater pressure would be applied by the screw unit 4 than intended), this becomes apparent from the visible end of the display element 4.2. This means that, through the display element 4.2, the user is clearly shown when a force predetermined by the length of the member 4.1, and by the embodiment of the spring 4.3, has been produced. Thus, by way of the visual signal, the user is better and more clearly prevented from further rotating the screw unit.

Depending on the embodiment of the upper end region of the display element 4.2, thus the region which becomes visible through the screwing-in of the screw 4, it is also possible to gradually draw conclusions concerning the force produced, or the screw-in depth attained.

FIG. 5 shows a further embodiment of the screw unit 4. This embodiment can also be generally used. In this case, a spring 4.17 is integrated into the screw unit 4, which spring pushes a pressure head 4.13 outward. If such a screw unit 4 is used, then an embodiment is possible which can dispense with the springs 12 in FIGS. 1 and 2; that is, such a screw unit 4 illustrated here can, for example, be screwed directly onto a section which is a part of the mounting-housing 5. The advantage is that the pressure head 4.13 is pushed out of the screw unit 4 by the force predefined by the spring 4.17, and is thus pressed against the mounting-housing 5. The screw unit 4 is screwed in up to a certain maximum abutment—more concerning this will follow—and the spring 4.17 inside the screw unit pushes the pressure head 4.13, with a defined force, outward; that is, in the direction of the pipeline. The spring 4.15 is markedly stiffer than the spring 4.17, and thus hardly contributes to the shifting of the pressure head 4.13.

The limiting unit 30 is formed here by a ratchet head 4.11 and a radial sawtooth assembly 4.18. In place of the sawtooth assembly 4.18, a ball-and-socket is possible, or it can be a sliding clutch. This ratchet head 4.11 permits the rotation of the screw unit 4 only up to a maximum angle, and thus to a maximum screw-in depth, or to the application of a maximum pressure force. The helical spring 4.15, for which spring-washer packs can also be used, provides a certain degree of compensation for temperature, or compensation for smaller mechanical changes of the geometry while in operation, such as the diameter of the pipe. A screw unit 4, as is shown in FIG. 5, can also be constructed with a display element 4.2, as in the preceding FIG. 4.

FIGS. 6a and 6b each show a section through a schematic illustration of the invention, with the screw-unit 4 being found in each case in a different condition. Here, the screw-unit 4 is composed of a excentric 4.20, which pushes a pin 4.21 through the bracket 6 in the direction of the spring 12. In FIG. 6a, the spring 12 is still slack, and in FIG. 6b it pushes with its compressive force in the direction of the pipeline. The excentric 4.20 is embodied in such a way that, in the case of its full actuation, the maximum pressure is applied, with which the sensor is pressed against the pipeline 15. The lever of the excentric 4.20 is embodied in such a way that a self-limiting feature results. This means that, in this embodiment, the screw-unit 4 and the limiting unit 30 are combined into a single unit.

LIST OF REFERENCE CHARACTERS

| | |
|---|---|
| 1 | tightening screw |
| 2 | guide bolts |
| 3 | knurling |
| 4 | screw unit |
| 4.1 | member |
| 4.2 | display element |
| 4.3 | spring |
| 4.4 | grub screw |
| 4.11 | ratchet head |
| 4.13 | pressure head |
| 4.14 | retaining ring |
| 4.15 | spring washer |
| 4.16 | disc |

-continued

LIST OF REFERENCE CHARACTERS

| | |
|---|---|
| 4.17 | helical spring |
| 4.18 | radial sawtooth assembly |
| 4.20 | excentric |
| 4.21 | pin |
| 5 | mounting-housing |
| 6 | bracket |
| 6' | passageway |
| 7 | cross piece |
| 8 | chain |
| 9 | band-clamp |
| 10 | standard retainer |
| 11 | coupling mat of elastomer or metal film |
| 12 | spring |
| 13 | medium |
| 14 | quick-locking securement catches |
| 15 | pipeline |
| 16 | measuring sensor |
| 17 | sensor roof |
| 18 | cylinder |
| 19 | coupling nut of plug |
| 20 | mounting screw |
| 21 | band bolt |
| 30 | limiting unit |
| 31 | abutment at the knurled nut |

The invention claimed is:

1. An apparatus for securing a sensor to a pipeline, the pipeline defining an axis, comprising:
a mounting-housing positionable on the pipeline;
at least one screw unit,
at least one spring; and
at least one limiting unit, which limits the screwing-in of said at least one screw unit, wherein:
said mounting-housing is embodied, and coordinated with the sensor, in such a manner that a force, which acts on said mounting-housing in the direction orthogonal to the axis of the pipeline, acts at least partly on the sensor in said direction orthogonal to the axis of the pipeline;
an adjustable force can be exerted on said mounting-housing in said direction orthogonal to the axis of the pipeline via said at least one screw unit;
said mounting-housing is coordinated with the sensor such that said mounting-housing lies at least partially on the end of the sensor facing away from the pipeline;
said mounting-housing and said at least one screw unit are embodied, and coordinated with one another, in such a manner that a screwing-in of said at least one screw unit into said mounting-housing exerts a force onto said mounting-housing directed essentially in the direction orthogonal to the axis of the pipeline;
said at least one screw unit exerts on said at least one spring a force directed essentially in the direction orthogonal to the axis of the pipeline or; and
the force which can be exerted on said mounting-housing and on the sensor in the direction of the directional orthogonal to the axis of the pipeline via said at least one screw unit is predetermined via the embodiment of said at least one spring.

2. The apparatus as claimed in claim 1, wherein:
said spring is a component of said at least one screw unit.

3. The apparatus as claimed in claim 1, wherein:
at least one movable bracket is provided in said mounting-housing; and
said bracket and said at least one screw unit are embodied, and coordinated with one another, in such a manner that a screwing-in of said screw unit in the direction of the pipeline produces a force on said bracket, which force is at least partially directed away from the pipeline.

4. The apparatus as claimed in claim 3, further comprising: at least one chain which can be placed radially around the pipeline, and which can be connected with said bracket.

5. The apparatus as claimed in claim 1, wherein: said limiting unit is embodied such that the limiting of the screwing-in of said at least one screw unit acts radially.

6. The apparatus as claimed in claim 1, wherein: the measuring sensor is an ultrasonic sensor.

7. An apparatus for securing a sensor to a pipeline, the pipeline defining an axis, comprising:
- a mounting-housing positionable on the pipeline;
- at least one screw unit;
- at least one spring; and
- at least one display element, wherein:
- said mounting-housing is embodied, and coordinated with the sensor, in such a manner that a force, which acts on said mounting-housing in the direction orthogonal to the axis of the pipeline, acts at least partly on the sensor in the direction orthogonal to the axis of the pipeline;
- an adjustable force can be exerted on said mounting-housing in the direction orthogonal to the axis of the pipeline;
- said mounting-housing is coordinated with the sensor such that said mounting-housing lies at least partially on the end of the sensor facing away from the pipeline;
- said mounting-housing and said at least one screw unit are embodied, and coordinated with one another, in such a manner that a screwing-in of said at least one screw unit into said mounting-housing exerts a force onto said mounting-housing directed essentially in the direction orthogonal to the axis of the pipeline;
- said at least one screw unit exerts on said at least one spring a force directed essentially in the direction orthogonal to the axis of the pipeline;
- said at least one screw unit is embodied in such a manner that said at least one display element indicates when a predetermined force has been produced with said at least one screw unit; and
- the force which can be exerted on said mounting-housing and on the sensor in the direction orthogonal to the pipeline via said at least one screw unit is predetermined via the embodiment of said at least one spring.

* * * * *